(12) United States Patent
Amoabediny et al.

(10) Patent No.: US 9,353,137 B2
(45) Date of Patent: May 31, 2016

(54) METHOD FOR SEPARATION AND PURIFICATION OF PHOSPHATIDYLCHOLINE EMPLOYING MAGNETIC NANOPARTICLES AND COMPOSITIONS SO PRODUCED

(71) Applicants: Ghassem Amoabediny, Tehran (IR); Sedigheh Khosrovaninia, Shiraz (IR); Mehdi Khoobi, Tehran (IR)

(72) Inventors: Ghassem Amoabediny, Tehran (IR); Sedigheh Khosrovaninia, Shiraz (IR); Mehdi Khoobi, Tehran (IR)

(73) Assignees: Ghassem Amoabediny, Tehran (IR); Sedigheh Khosrovaninia, Shiraz (IR)

( * ) Notice: Subject to any disclaimer, the term of this patent is extended or adjusted under 35 U.S.C. 154(b) by 0 days.

(21) Appl. No.: 14/614,148

(22) Filed: Feb. 4, 2015

(65) Prior Publication Data
US 2015/0225429 A1   Aug. 13, 2015

Related U.S. Application Data

(60) Provisional application No. 61/936,875, filed on Feb. 7, 2014.

(51) Int. Cl.
*C07F 9/10*   (2006.01)

(52) U.S. Cl.
CPC .................................... *C07F 9/103* (2013.01)

(58) Field of Classification Search
None
See application file for complete search history.

(56) References Cited

U.S. PATENT DOCUMENTS

| | | | |
|---|---|---|---|
| 1,053,299 A | | 2/1913 | Knowles |
| 2,945,869 A | | 7/1960 | Myer et al. |
| 3,544,605 A | | 12/1970 | Betzing et al. |
| 4,235,793 A | * | 11/1980 | Betzing .................. C07F 9/103 554/83 |
| 4,443,378 A | | 4/1984 | Gunther |
| 4,452,743 A | | 6/1984 | Gunther |
| 4,714,571 A | * | 12/1987 | Tremblay ................ C07F 9/103 426/614 |
| 4,814,111 A | * | 3/1989 | Kearns ..................... C07F 9/103 554/83 |
| 5,429,823 A | * | 7/1995 | Tremblay .................. A23J 7/00 424/1.21 |
| 5,453,523 A | * | 9/1995 | Weete ..................... C07F 9/103 554/10 |
| 2013/0129634 A1 | * | 5/2013 | Tampieri ............ A61K 49/0002 424/9.36 |

FOREIGN PATENT DOCUMENTS

| | | | | |
|---|---|---|---|---|
| CH | 561088 | | 4/1975 | |
| CN | 101703917 A | * | 5/2010 | ............ C02F 101/20 |
| CN | 103254226 A | * | 8/2013 | ............. B01D 15/08 |

OTHER PUBLICATIONS

CN 103254226 A, Ren Qilong, et al., Mehod for separating and purifying lecithin through fixed-bed adsorpton mehod, 2013, English translation, 16 pages.*

(Continued)

*Primary Examiner* — Yate K Cutliff
(74) *Attorney, Agent, or Firm* — Van Dyke Law; Raymond Van Dyke

(57) ABSTRACT

A process for separation and purification of phosphatides, especially phosphatidylcholine, from vegetable lecithins, comprising deoiling with acetone, dissolved in alcoholic solvent and then treated with magnetic nanoparticles as sorbent, in order to adsorb non-choline phosphatides, and the purified phosphatidylcholine-rich composition derived therefrom.

15 Claims, 4 Drawing Sheets

(56) References Cited

OTHER PUBLICATIONS

Hardani, Kh, et al, Removal of toxic mercurh (II) from water via Fe3O4/hydroxyapatite nanoadsorbent: an efficient economic and rapid approach, 2015, American Associatin for Science and Technology Journal of Nanoscience, 1(1) pp. 11-18.*

CN 101703917 A, Chen Y, et al., Magnetic nono-0hydroxyapatite adsorbent for removing heavy metal ions, e.g. copper, in wastewater comprises nano-hydroxyapatite as matrix, and magnetic powder iron oxide that is uniformly dispersed in matrix, 2010, 7pages.*

* cited by examiner

METHOD FOR SEPARATION AND PURIFICATION OF PHOSPHATIDYLCHOLINE EMPLOYING MAGNETIC NANOPARTICLES AND COMPOSITIONS SO PRODUCED

CROSS REFERENCE TO RELATED APPLICATION

The present invention claims priority from pending U.S. Provisional Patent Application Ser. No. 61/936,875, filed Feb. 7, 2014, entitled "Method for separation and purification of phosphatidylcholine based on magnetic nanoparticles," the subject matter of which is incorporated by reference herein in its entirety.

SPONSORSHIP STATEMENT

This application has been sponsored by the Iranian Nanotechnology Initiative Council, the School of Chemical Engineering, College of Engineering, University of Tehran, and the Research Center for New Technologies in Life Science Engineering, University of Tehran, all of which do not have any rights in this application.

BACKGROUND OF THE INVENTION

In the fats and oils industry, the term "lecithin" is used to refer to a complex mixture of phosphatides that include various classes of compounds based on differences in the polar groups of molecular structures, such as phosphatidylcholine (PC), phosphatidylethanolamine (PE), phosphatidylinositol (PI), phosphatic acid (PA) and other substances, such as triglycerides, carbohydrates, etc. In the scientific literature, "lecithin" is often regarded as referring to phosphatidylcholine or PC. The industry use of the term lecithin is applied herein, and the various names for specific phosphatides, such as PC, PE, etc., will be used.

Phosphatidylcholine is used extensively in the pharmaceutical industry, and highly pure PC is quite important for this industry. Recognition of the unique properties and possible uses of individual phosphatide components of lecithin, particularly PC, and the adverse effects in some applications containing contaminating non-choline phosphatides in PC-enriched fractions, have stimulated the search for improved methodologies for PC purification from lecithin.

There are many known methods for obtaining highly-purified phosphatidylcholines from various raw materials. For example, Swiss Pat. No. 561,088 and U.S. Pat. No. 2,945,869 set forth purification processes of soya phosphatidylcholine, which are to be used as emulsifiers for intravenous applications. Alcoholic solutions of previously de-oiled raw phosphatides are treated with $Al_2O_3$, MgO and/or activated carbon in order to make these solutions free of cephalins, and especially to reduce, as far as possible, the inositol-containing phosphatides, which have been found to lower the blood pressure in cats when introduced intravenously. However, this procedure always first required removal of the oil from the commercially-available, crude phosphatide prior to the preparation of the alcoholic solutions, which will only lead to a reduction in the cephalin content, regardless of the absorbent being used. The results for such processes demonstrate product purities not exceeding 70%. Accordingly, the complete removal of the cephalin cannot be accomplished by this method.

U.S. Pat. No. 3,544,605 describes a process to obtain highly-purified PC with a high content of essential fatty acids, which is free of, or heavily depleted in, cephalins, from plant lecithin by adsorption of the phosphatides on aluminum oxide and extraction with alcohol. In this process, the crude oil-containing phosphatide is first dissolved in ethyl acetate or a di-chlorinated hydrocarbon having 1 to 4 carbon atoms or a mixture of solvents (without prior de-oiling). The solution is then treated, with stirring, with at least a five-fold amount of aluminum oxide relative to the content of raw phosphatide, or may be carried out by adding the solution to an aluminum oxide column (instead of stirring therewith). Finally, the highly-purified, oil-free PC is liberated with alcohol from the separated aluminum oxide.

German Pat. No. 1,053,299 sets forth a process for obtaining natural choline phosphoric acid diglycerid esters, which are free of colamin, by using an aluminum oxide column chromatography treatment. Here again, an alcoholic extract of the previously de-oiled raw phosphatide, with the prior removal of oil, is achieved by repeated extraction with acetone.

U.S. Pat. No. 4,235,793 describes a process where raw lecithin is first extracted with alcohol. The resulting two phases are separated and the alcohol-rich upper phase is treated with aluminum oxide adsorbent. Elution of the adsorbent with an alcohol leads to an oily phosphatidylcholine, free of cephalin.

U.S. Pat. No. 4,443,378 is related to a method for the separation of acylated phospholipids. This process involves chromatography on a silicic acid gel in a lower alkanol containing 1 to 4 carbon atoms.

Finally, U.S. Pat. No. 4,452,743 is related to a method for the separation of oil and/or phosphatidylethanolamine from alcohol-soluble, phosphatidylcholine products containing the same. This process also involves chromatography on a silicic acid gel in a lower alkanol containing 1 to 4 carbon atoms.

Recently, one of the most important uses of PC involves PC becoming the primary functional ingredient of liposomes, where stable liposomes are formed with high-PC preparations. In order to obtain the best liposomes, 80 to 100% purity PC is required, rendering all of the aforesaid prior art techniques discussed herein inadequate.

Today, column chromatography is considered more appropriate for industrial purification of phosphatides. Chromatographic means are, however, generally slow and costly. On large scales especially, the large quantity of column packing required and the high associated instrumentation costs limit the use of column chromatography to the separation and purification of only the most valuable and expensive compounds. To reduce this cost, many researches have done a great deal of the work, but the results have not been satisfactory.

Therefore, it is an objective of the instant invention to provide more economical approaches and methods for the purification of phosphatidylcholine, and generate purer forms of phosphatidylcholine and like compositions using the aforesaid improved techniques and approaches.

These and many other objects are met in various embodiments of the present invention, offering significant advantages over the known prior art.

SUMMARY OF THE INVENTION

In accordance with the foregoing and other objectives, set forth herein is a description of an improved process for removing non-choline phosphatides to facilitate obtaining a more purified phosphatidylcholine product, and the products so produced. The product can be obtained efficiently even when starting with a raw soybean gum (lecithin). In addition, in the present invention $Fe_3O_4$ magnetic nanoparticles coated with hydroxyapatite are used as sorbents to fractionate phosphatides, especially for purifying phosphatidylcholine from a mixture of phosphatides.

A magnetic solid-phase extraction (SPE) method has been developed and applied for bio-separation and chemical analyses by many researchers. In this method, paramagnetic sorbents are dispersed in solution to adsorb the targets, and then collected by an external magnet for elution, which greatly simplifies the SPE procedure. Among different kinds of magnetic nanoparticles, magnetite ($Fe_3O_4$) has developed into an interesting and useful advanced material due to its unique physical and chemical properties.

The magnetic nanoparticles, as employed in the present invention, may be used alone, coated or complexed with one or more special-functional ligands that enhance the selectivity or the affinity of target molecules to the nanoparticles.

In one disclosed embodiment of a process of the present invention, the magnetic particles are mixed with the solutions containing the impurities for a sufficient period, allowing the magnetic particles to form a complex or conjugate with the target.

Subsequent to the intended separation, extraction could be performed by an external magnetic field of sufficient strength. The liquid portion, free of the nanoparticles and the bound target, is then separated from the portion of the solution containing the nanoparticles.

The nanoparticles, complexed or conjugated with the target, are regenerated by subjecting them to conditions which result in the release of the target from the nanoparticles, thereby freeing them for further use.

Where the target itself is a valuable molecule, the released target is collected for use in any further processing. The regenerated nanoparticles are thus suitable for reuse in the above described process.

In a preferred embodiment of the present invention, lecithin was removed from natural lipids by precipitation in a ketone solvent, such as acetone.

Phosphatidylcholine is then solubilized in an alcohol solvent, preferably ethanol. Final purification was achieved by adsorption of non-choline phosphatide on functionalized magnetic nanoparticles.

The nanoparticles are mixed with the ethanolic solution of lecithin, which mainly contains PE, PC and small quantities of PI, which permits binding of the phosphatides, except phosphatidylcholine, to the functionalized particles. Under low magnetic fields (about 1 Tesla), the molecules bound with the magnetic nanoparticles are attracted and separated by using external magnets.

The process disclosed within the present invention is simple, efficient, rapid and entails inexpensive instruments compared to the referent prior art. The process of the present invention readily permits the achievement of purities greater than 87%, making the teachings of the instant invention useful for the aforementioned liposome PC purity requirements and other uses.

Additionally, the process of the present invention eliminates the use of column chromatography for the purification of PC. The present invention is instead based in one embodiment on multiple extractions performed sequentially using acetone or supercritical $CO_2$, ethanol and adsorption impurities on magnetic nanoparticles.

Furthermore, other equipment, such as a high gradient magnetic separation (HGMS) system, magnetic filter or magnetic solid phase extraction column, can be employed herein. These are state-of-the-art unit operations currently used throughout the industry. Economic estimations show that the costs for the methods conducted pursuant to the present invention are less than those for the aforementioned chromatographic methods, making the instant invention quite cost-effective in operations.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

DETAILED DESCRIPTION OF THE INVENTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Nanotechnology combined with magnetic separations have already drawn enormous attention in areas as diverse as biosensors, magnetic targeted drug delivery, novel diagnostic devices, cell separations, as well as other health-related applications. The present invention is principally based on separation by magnetic adsorbent.

Iron-containing nanoparticles are the preferred magnetic nanomaterial for such applications since they are non-toxic and have already been approved by the U.S. Food and Drug Administration as a contrast MRI agent. Central to the success of magnetic nanoparticles is the maneuverability of magnetic nanoparticles by applying magnetic fields that overcome opposing forces, such as Brownian motions, viscous drag and sedimentation. An advantage of magnetic sorbents is that they may be recovered from the system without filtration, with the help of an external magnetic field. Selective removal of target compounds from complex matrixes can thus be obtained, such as where certain special functional ligands with affinity for target molecules are bounded onto the magnetic nanoparticles. The present invention relates to methods of using such magnetic nanoparticles for selectively removing non-choline phosphatides of interest to produce a purified phosphatidylcholine, especially for pharmaceutical applications.

Figure 1:
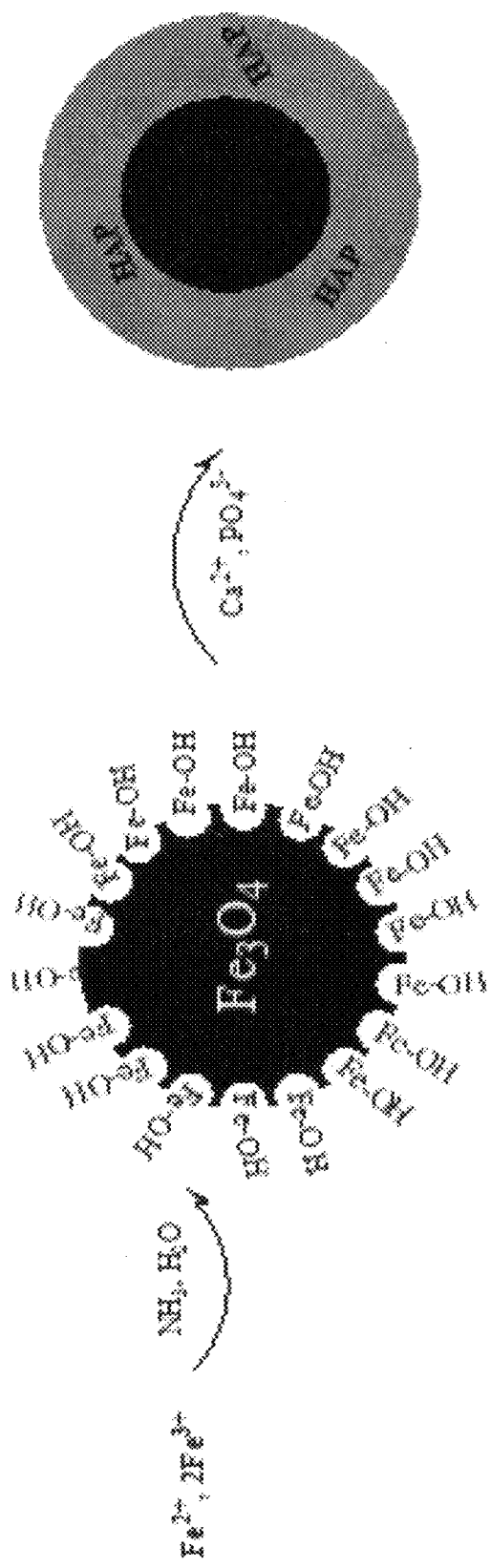
FIG. 1 generally illustrates the manufacture or creation of magnetic nanoparticles, and then the cross-linking of the generated nanoparticles to hydroxyapatite (HAP), a construct which is used pursuant to the teachings of the present invention.

Magnetic nanoparticles may be synthesized by various known techniques and methods, where paramagnetic nanoparticles are preferred, and super-paramagnetic nanoparticles are most preferred herein. An exemplary technique for the construction or manufacture of iron-containing nanoparticles with a hydroxyapatite coating is shown in FIG. 1 of the DRAWINGS, which generally demonstrates steps for the building of a magnetically-inducible iron core from iron molecules, such as magnetite, and the subsequent covering or coating of the iron core with hydroxyapatite, as illustrated, to form the aforementioned hydroxyapatite (HAP) coated magnetic nanoparticles (MNP).

The nanoparticles can be synthesized using a known methodology for the thermal decomposition of a metal precursor: thermal decomposition in the presence of a stabilizing ligand as a surfactant, and co-precipitation with or without a stabilizing ligand as a surfactant.

A co-precipitation method used can be seen in the first Example discussed in more detail hereinbelow. This method can also be used in the presence of a stabilizing ligand surfactant.

Reaction conditions are selected to produce particles in a size range of from about 1 to 500 nm, preferably from about 1 to 50 nm, most preferably from about 1 to 20 nm.

The nanoparticles are preferably mono-dispersed after synthesis to facilitate further processing and maintain a high surface area to volume ratio. The addition of surfactants that are surface active agents facilitates such dispersion.

The magnetic nanoparticles may be used as such, or surface functionalized with a coating. The magnetic nanoparticles may be coated to enhance specificity and/or affinity to the specific target.

A starting material for the present invention is lecithin. Lecithins are commercially available in a wide variety of products. For example, mixtures with vegetable oil, fractionated forms that are enriched in particular phosphatides, chemically modified forms, etc. The preferred source material for the present invention is soybean lecithin. It should, of course, be understood, however, that any suitable, commercially-available source of lecithin can be used in practicing the principles of the instant invention.

The source materials so obtained can be treated with any known methods to remove extraneous substances which might hinder the purification, such as proteins, carbohydrates, and triglycerides. Then, as a first step in processing, raw gum lecithin is precipitated with cold acetone. The amount of solvent employed is generally in the range of about 5:1 in volume of solvent (ml) to weight of lecithin (gram). It is understood that for this separation that phosphatides are insoluble in acetone, while the oils are soluble in acetone, thus allowing extraction of the oils from the insoluble phosphatides. It should also be understood that such an extraction could be carried out by using supercritical $CO_2$ instead of acetone to remove the oils and pigments.

Acetone is then added to the raw gum lecithin at room temperature and stirred for 4 hours. The acetone insoluble fraction was allowed to cool down to about 0 to 5° C. and maintained at that temperature for about 1 hour with stirring. Then it was filtered with suction in a Buchner funnel. The acetone insoluble fraction was then dried under reduced pressure and low temperature in a freeze drier for about 24 hours.

When phosphatides are extracted or isolated from main origin (bio-membranes), polymorphism can occur, which refers to the formation of diverse structures (bilayer, micelle, non-bilayer). Ethanol has been recognized as being an excellent solvent in an aqueous solution for inducing non-bilayer phases in phosphatides. The formation of non-lamellar phases in phosphatides is not completely understood, but it is significant that this amphiphilic molecule is capable of doing so. Also, ethanol can be fractionated phosphatidylcholine and phosphatidylinositol because of their dissimilar solubility in ethanol. Phosphatidylcholine, however, is relatively more soluble in ethanol than is phosphatidylinositol.

To prepare the ethanol-soluble fraction, the acetone insoluble is dissolved in ethanol (99%) with an ethanol/acetone insoluble ratio of about 6:1. The solution is stirred for about 10 minutes at room temperature, and then centrifuged at about 10,000 rpm for about 10 minutes. The ethanol-soluble fraction was combined and stored at about 0° C. for solid phase extraction.

Since the phosphatides have similar structures, with slight differences in their polar head groups, choosing a suitable coating to act as the sorbent is important and challenging. Therefore, the Applicants herein tested a coating with a network of positive and negative ions to investigate the absorption through ion interaction. In certain embodiments, hydroxyapatite was used as a surface functionalized coating for adsorption of non-choline phosphatides onto magnetic nanoparticles, such as generally illustrated and described in connection with FIG. 1.

A co-precipitation method was used to synthesize superparamagnetic iron oxide nanoparticles, whereby a solution of $FeCl_2$ and $FeCl_3$ were mixed in water and added to about 25% $NH_4OH$. A black precipitate is formed immediately, and the reaction is left to react for about 1 hour at room temperature to about 37° C. Nanoparticles are decanted, where a permanent magnet or centrifugation is used to separate the nanoparticles. The nanoparticles were washed 3 to 5 times by deionized water. No stabilizers were used for the solution, and the nanoparticles were bare. The bare magnetic nanoparticles are characterized by the aforementioned scanning electron microscope (SEM) and transmission electron microscopy (TEM) imaging.

Co-precipitation synthesis equation:

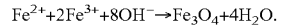

$$Fe^{2+}+2Fe^{3+}+8OH^-\rightarrow Fe_3O_4+4H_2O.$$

Figures 2A, 2B:
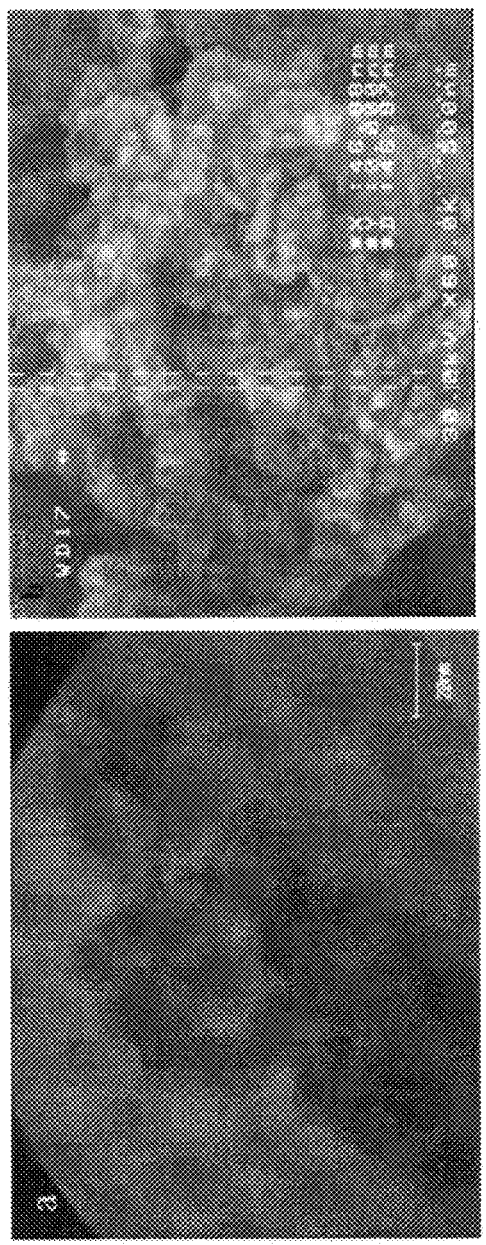
FIGS. 2A and 2B depict two images, where a) illustrates a transmission electron microscopy (TEM) image of $Fe_3O_4$, and b) illustrates a scanning electron microscope (SEM) image of magnetic nanoparticles coated with hydroxyapatite pursuant to the principles of the present invention.

The average size could be distinguished about 20 nm for bare magnetic particles, as shown in FIG. 2A of the DRAWINGS. The modification by hydroxyapatite led to the increased the size. According to the SEM image, the dimension of the hydroxyapatite-coated magnetic nanoparticle (MNP) is less than about 70 nm with an almost spherical and uniform morphology, as illustrated in FIG. 2B of the DRAWINGS.

It should be understood that the mechanism for the adsorption of phosphatides by sorbents is complicated, and also has been described as a "mixed-mode" ion exchange. The mechanism involves nonspecific interactions between positively-charged calcium ions and negatively-charged phosphate ions on the stationary-phase hydroxyapatite with phospholipid negatively-charged carboxyl groups and positively-charged amino groups. Therefore, the expected phosphatidylethanolamine and phosphatidylinositol interacted with the hydroxyapatite.

Figures 3A, 3B:
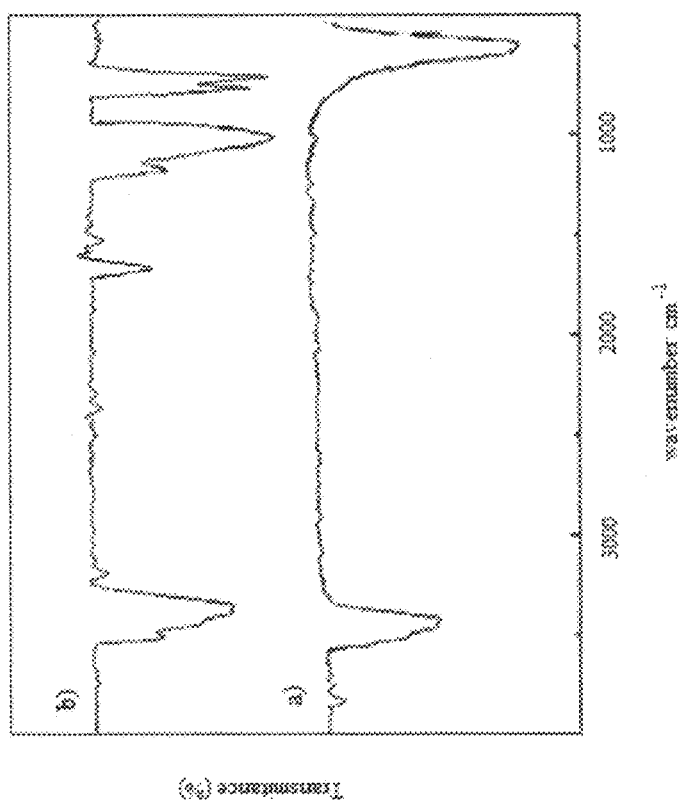
FIGS. 3A, 3B and 3C depict three images for Fourier transform infrared spectroscopy (FT-IR) spectra of a) $Fe_3O_4$, b) magnetic nanoparticles coated with hydroxyapatite, and c) the admixture after adsorption of phosphatides by the magnetic nanoparticles, with various inflection or peak points identified, each pursuant to the teachings of the present invention.

Shown in FIG. 3 of the DRAWINGS are three images of Fourier transform infrared spectroscopy (FT-IR) spectra. The FT-IR studies shown in FIG. 3 have been performed in the range of 400 to 4000/cm-1 for identification of various functional groups. With reference to FIG. 3A, there is shown a spectra for $Fe_3O_4$, identifying the inflection or peaks corresponding to the $Fe_3O_4$ such as in the iron core or magnetite, as depicted in FIG. 1. Similarly, FIG. 3B illustrates the spectra for the aforementioned magnetic nanoparticles coated with hydroxyapatite, identifying the inflection or low points corresponding thereto.

Figure 3C:
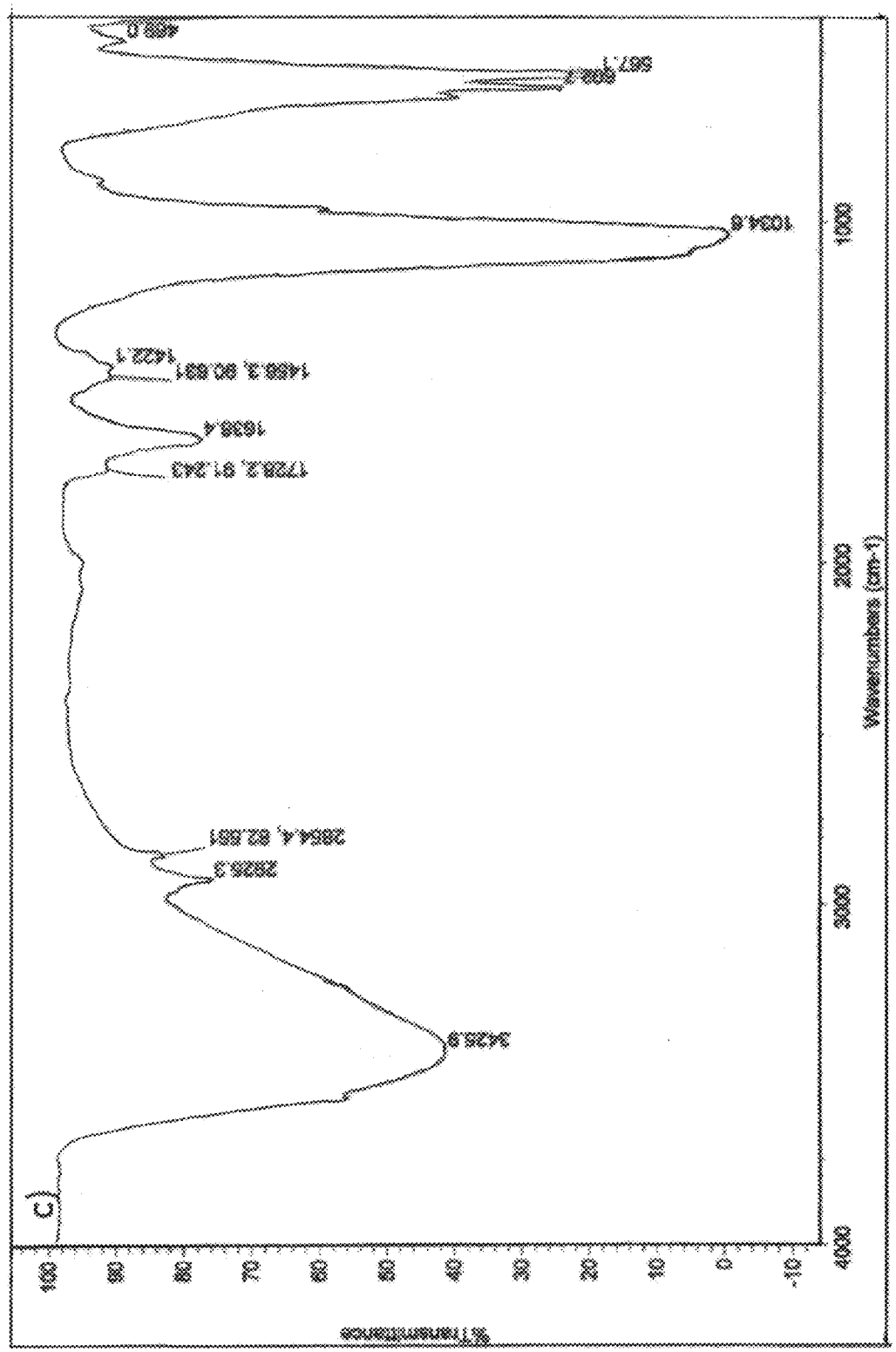

Finally, FIG. 3C illustrates the spectra for the resultant admixture of the HA-coated iron core after adsorption of phosphatides by the magnetic nanoparticles, with various inflection or peaks identified. Indeed, the FT-IR spectra of the resultant admixture shows several major peaks, located, for example, at 3,425.9; 2,925.3; 2,854.4 (with 82.551% transmittance); 1,728.2 (with 91.243% transmittance); 1,638.4; 1,456.3 (with 90.631% transmittance); 1,422.1; 1,034.5; 602.7; 567.1 and 469.0 $cm^{-1}$.

It should, of course, be understood that the quantity of nanoparticles per liter of solution from which the target is to be removed depends upon the amount of the target in the solution.

It will be understood by these versed in the separation arts that the quantity of nanoparticles to be used is also a function of the amount of target present in the solution. Where a solution is diluted, the quantity of nanoparticles should be at least about 0.05 gr for about 10 mg/l phosphatides.

In one embodiment of the present invention removing non-choline phosphatides from lecithin is quite useful. Therefore, the ethanolic solution lecithin is mixed with hydroxyapatite-coated magnetic nanoparticles at temperature of from about 20° C. to 60° C., preferably at a temperature of about 30° C. to 40° C. for a period of from about 10 to 60 minutes. After applying an external magnet, the liquid portion is collected and dried under an inert gas such as Argon.

EXAMPLES

Phospholipids Sample Preparation

In the first set of experiments, lecithin is blended with dry acetone (about 1:5) at room temperature, cooled down to about 0 to 5° C. for about 1 hour and then filtered with suction in a Buchner funnel. The filtrate cake is again blended, as above, and the filter cake is dried under reduced pressure and low temperature in a rotary vacuum evaporator. The residue was fractionated with ethanol (99%) in an ethanol/de-oiled gum ratio of about 6:1 to produce the aforementioned soluble (ES) and insoluble (EI) fractions. The ES fraction was combined and stored at about 0° C. for the aforesaid solid-phase extraction (SPE) progress.

Synthesis of the Nanoparticles

A complete precipitation of $Fe_3O_4$ is achieved under alkaline conditions, while maintaining a molar ratio of $Fe^{2+}$: $Fe^{3+}$ = 1:2 under a non-oxidizing environment. To obtain 1 g of $Fe_3O_4$ precipitate, 0.86 g of $FeCl_2.4H_2O$ and 2.36 g of $FeCl_3.6H_2O$ were dissolved under Argon in about 40 ml of deionized water with vigorous stirring (about 1,000 rpm). The resulting solution was added drop wise to a 25% NH4OH solution (about 10 mL). After about 15 min, 100 mL of $Ca(NO_3)_2.4H_2O$ (33.7 mmol) and $(NH_4)_2HPO_4$ (20 mmol) solutions adjusted to pH 11 were added drop wise to the obtained precipitate over about 30 min with mechanical stirring. The resultant milky solution was heated to about 90° C. After about 2 hours, the mixture was cooled to room temperature and aged overnight. The dark brown precipitate formed was filtered, washed repeatedly with deionized water, and dried under vacuum at about 70° C. temperature.

Magnetic SPE Procedure 0.2 gr nanoparticles sorbents were dispersed into an ethanolic lecithin solution by 10 mg/ml concentration for about 1 min with a probe sonicator (ultrasonic liquid processor), and immediately mixed with moderate agitation for about 20 min at about 38° C. and at pH 6.5, and then magnetic nanoparticles were separated by applying an external magnet. Finally, the supernatant was dried under Argon gas for phosphatides analysis, which indicated that a purity of phoshatidylcholine at 87% was reached. It should be understood that the technique of the instant invention can be employed multiple times for better separation and extraction of the phosphatidylcholine. Accordingly, high purities of about 85-100% are possible, where ranges of purity of 85-90, 85-95, 90-95, 90-100 are possible dependent on the conditions employed and the number of iterations.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the breadth or scope of the applicant's concept. Furthermore, although the present invention has been described in connection with a number of exemplary embodiments and implementations, the present invention is not so limited but rather covers various modifications and equivalent arrangements, which fall within the purview of the appended claims.

What is claimed is:

1. A process for purifying phosphatidylcholine comprising:

mixing a plurality of magnetic nanoparticles coated with hydroxyapatite into a phosphatide mixture, said phosphatide mixture containing phosphatidylcholine and non-choline phosphatides, said hydroxyapatite on said magnetic nanoparticles adsorbing said non-choline phosphatides;

applying a magnetic field to a resultant solution; and separating, after application of said magnetic field, the magnetic nanoparticles coated with hydroxyapatite with the adsorbed non-choline phosphatides from the resultant solution, whereby said process does not involve chromatographic solid phase extraction.

2. The process according to claim 1, wherein said phosphatide mixture is derived from a lecithin-containing material, said lecithin-containing material precipitated from a natural lipids solution using a ketone solvent.

3. The process according to claim 2, wherein said ketone solvent is acetone.

4. The process according to claim 2, wherein said precipitated lecithin-containing material is solubilized in an alcohol solvent, resulting in said phosphatide mixture.

5. The process according to claim 4, wherein said alcohol solvent is ethanol.

6. The process according to claim 2, wherein said lecithin-containing material comprises soybean gum.

7. The process according to claim 1, wherein, during said mixing, non-choline phosphatides are adsorbed by said magnetic nanoparticles coated with hydroxyapatite.

8. The process according to claim 1, wherein, during said mixing, cationic phosphatides in said phosphatide mixture are adsorbed onto said magnetic nanoparticles containing the hydroxyapatite.

9. The process according to claim 1, wherein a solid phase of said plurality of magnetic nanoparticles coated with hydroxyapatite is selected from the group consisting of apatite powder, apatite nanoparticles, magnetic nanoparticles coated by apatite, and combinations thereof.

10. The process according to claim 1, wherein the hydroxyapatite in the adsorbent constitutes about 40 percent to about 95 percent of the adsorbent by weight.

11. The process according to claim 1, further comprising:
   eluting the adsorbed non-choline phosphatides from the resultant solution,
whereby purified phosphatidylcholine remains.

12. The process according to claim 1, further comprising:
   extracting, after said separating, a supernatant from the resultant solution.

13. The process according to claim 12, further comprising: drying said supernatant under Argon.

14. The process according to claim 1, further comprising:
   decoupling, after said separating, the magnetic nanoparticles coated with hydroxyapatite from the adsorbed non-choline phosphatides, and
separating and recovering the magnetic nanoparticles,
thereby regenerating the magnetic nanoparticles for further use.

15. The process according to claim 14, further comprising:
   extracting a phosphatide from the decoupled non-choline phosphatides.

\* \* \* \* \*